United States Patent [19]

Reid

[11] Patent Number: 4,552,845

[45] Date of Patent: Nov. 12, 1985

[54] METHOD FOR SEPARATING LYSOZYME FROM EGG-WHITE

[76] Inventor: Lorne S. Reid, 3304 W. Third Ave., Vancouver, British Columbia, Canada, V6R 1L4

[21] Appl. No.: 439,408

[22] Filed: Nov. 5, 1982

[51] Int. Cl.$^4$ .......................... C12N 9/36; C07G 7/00; C08L 5/00
[52] U.S. Cl. .................................. 435/206; 260/121; 260/122; 106/205
[58] Field of Search ................. 435/206; 260/121, 122

[56] References Cited

PUBLICATIONS

Chibata et al., Journal of Chromatography, vol. 215, pp. 93–98, (1981).
Muzzarelli et al., Biotechnology and Bioengineering, vol. XX, pp. 87–94, (1978).
Cherkasov et al., Molekulyarnaya Biologia, vol. 1, No. 1, pp. 41–46, (1967).
Jensen et al., Eur. Journal of Biochemistry, vol. 26, pp. 305–312, (1972).

Primary Examiner—Lionel M. Shapiro
Attorney, Agent, or Firm—Seed and Berry

[57] ABSTRACT

The present invention relates to a method for separating lysozyme from egg-white which has a lysozyme fraction and an albumin fraction, without destroying the commercial utility of the lysozyme fraction or the albumin fraction. The method comprises the step of preferentially, reversibly binding the lysozyme fraction of the egg-white to an affinity resin at about the natural pH of the egg-white by contacting the egg-white with the resin, separating the albumin fraction from the resin to leave the lysozyme fraction bound to the resin in a lysozyme-resin complex, and eluting the bound lysozyme from the resin to obtain a lysozyme solution and a reusable resin. The eluted lysozyme and the separated albumin fraction are further treated in separating processing lines to produce a commercial albumin fraction egg-white product and a commercial lysozyme product. The invention also deals with the preparation and compositions of suitable affinity resins for the reversible, preferential binding of lysozyme in egg-white.

32 Claims, 2 Drawing Figures

METHOD FOR SEPARATING LYSOZYME FROM EGG-WHITE

DESCRIPTION

TECHNICAL FIELD

The present invention relates to a method for separating lysozyme from egg-white, particularly with the use of an affinity resin to bind the lysozyme preferentially.

REFERENCE TO RELATED DOCUMENTS

I. Lysozyme Processing
  1. U.S. Pat. No. 3,515,643, entitled "PROCESS FOR THE PRODUCTION OF LYSOZYME"
  2. U.S. Pat. No. 3,419,471, entitled "PREPARATION OF ALBUMIN-FREE LYSOZYME"
  3. U.S. Pat. No. 2,579,455, entitled "CRYSTALLIZATION OF LYSOZYME FROM EGG-WHITE"

II. Lysozyme Derivatives
  1. U.S. Pat. No. 3,937,815, entitled "LYSOZYME DERIVATIVES"
  2. U.S. Pat. No. 3,859,435, entitled "BASIC DERIVATIVES OF LYSOZYME"

III. Enzyme Isolation
  1. U.S. Pat. No. 3,184,394, entitled "PROCESS FOR THE PREPARATION OF ENZYMES, TOXINS AND TOXOIDS"

IV. Articles
  1. Muzzarelli et al., ISOLATION OF LYSOZYME ON CHITOSAN, *Biotechnology and Bioengineering*, Vol. XX, 87–94 (John Wiley & Sons, Inc. 1978).
  2. Jensen and Kleppe, STUDIES ON T4 LYSOZYME: AFFINITY FOR CHITIN AND THE USE OF CHITIN IN THE PURIFICATION OF THE ENZYME, 26 *Eur. J. Biochem.* 305–312 (1972).
  3. Cherkasov et al., ISOLATION AND PURIFICATION OF LYSOZYME BY FRACTIONATION ON A CHITIN COLUMN, translated from Molekulyarnaya Biologiya, Vol. 1, No. 1, 41–46 (January–February, 1967).
  4. Weaver et al., DEAMINATED CHITIN AFFINITY CHROMATOGRAPHY: A METHOD FOR THE ISOLATION, PURIFICATION AND CONCENTRATION OF LYSOZYME, *J. Food Sci.*, Vol. 42, No. 4, 1084–1087 (1977).
  5. Tosa et al., IMMOBILIZATION OF ENZYMES AND MICROBIAL CELLS USING CARRAGEENAN AS MATRIX, *Biotechnology and Bioengineering*, Vol. XXI, 1697–1709 (John Wiley & Sons, Inc., 1979).
  6. Chibata et al., APPLICATION OF CARRAGEENAN BEADS FOR CHROMATOGRAPHIC PURIFICATION OF PROTEINS, *Journal of Chromatography*, CHROM. 13,959 (1981).

BACKGROUND ART

Lysozymes are a unique class of enzymes which can be extracted from a variety of organic sources, but most profitably from hen egg-whites (HEW). Physical and biochemical aspects of HEW lysozyme have been extensively researched since lysozyme was first discovered by Sir Alexander Fleming in 1922. This analysis has shown that lysozyme is a small but hardy enzyme which has a potent antibacterial action (which accounts for its current pharmaceutical importance).

Work involving use of lysozyme in foods has been conducted mainly in Japan. Lysozyme can be used on food packaging films to render the films antiseptic, and can be added to foods, such as sausages, other meats, and dried milk compositions, to serve as a preservative.

Purified lysozyme or its salts are of decided commercial value in Japanese and world markets. Certain investigators have claimed that lysozymes are beneficial in the treatment of cancers. Continuing research and interest in lysozymes encourages the development of a commercial method to isolate quantities of the proteins.

Egg-white consists of a mixture of nearly pure protein having ovalbumin, conalbumin, ovomucoid, lysozyme, ovomucin, flavoprotein-apoprotein, "proteinase inhibitor," avidin, other proteins, and nonproteins. The other proteins mainly include globulins, while the nonproteins are primarily glucose and poorly characterized salts. For purposes of this description, egg-white may be characterized as being a lysozyme fraction (consisting essentially of lysozyme) and an albumin fraction (consisting of the other proteins and nonproteins). In this description, "albumin" is used to describe the bulk of the egg white and is intended to be synonomous with "albumen," which is also commonly used as a noun for the egg white. The "albumin fraction" is the egg white remaining after extraction of the lysozyme.

Lysozyme is an enzyme, and causes cell lysis (dissolution) by breaking bonds in carbohydrate polymers found in the cell walls. Lysozyme has antibiotic activity. In egg-white, lysozyme is the active ingredient to protect the embryo against microbial factors.

HEW lysozyme is a basic protein of pI 10.5, molecular weight approximately 14,000 Daltons, and $S_{20,W}$ value of 1.9. H. FEVOLD, ADVANCES IN PROTEIN CHEMISTRY, 6, 188–252 (1951). The lysozyme apparently cleaves the beta-glucosidic linkage between the C1 of N-acetylmuramic acid and the C4 of N-acetylglucosamine polymers.

Lysozymes are used clinically as antibacterialitic agents against infectious diseases, therapeutic agents in the treatment of wounds, and potentiators of many antibiotics. That is, lysozyme increases the effect of the antibiotics and allows lower concentrations of antibiotics to act for longer periods of time.

Because dried egg-whites are commercially valuable apart from the lysozyme, it is important that a commercial method be developed to allow the extraction of the lysozyme while retaining the commercial value of the remaining egg-white. Furthermore, a desirable method would include use of a reusable resin of the affinity type to allow recovery of the lysozyme at a reduced cost. Because lysozyme is capable of cleaving the NAM-NAG bond of murein to cause cell lysis, immobilizing lysozyme on an affinity resin often leads to hydrolysis of the resin. A resin to which lysozyme could be reversibly bound would provide a foundation for a commercially valuable process for the separation of lysozyme from egg-white.

U.S. Pat. No. 3,515,643 discloses a process for the production of lysozyme which consists of contacting the egg-white with a weakly acidic ion-exchange resin at a pH of 6–7 to preferentially bind the lysozyme by ionic action. Preferred exchange resins are "Amberlite CG-50" and "Amberlite IRC-50." (Both are methacrylic carboxylic acid resins obtainable from Rohm and Haas Company. "Amberlite" is a registered trademark.) Ion-exchange resins differ markedly in their mechanism of action from that of affinity resins. Ion-exchange resins work on the basis of electrostatic charge, while affinity resins work on the basis of chemical structure.

U.S. Pat. No. 3,419,471 discloses a method for preparation of albumin-free lysozyme using an ion-exchange filtration method. Anion exchange cellulose or anion exchange dextran previously buffered with a buffer solution of the same pH and ionic strength as the enzyme solution to be treated are used in one step of the process. Suitable anion exchange celluloses include GE-cellulose, TEAE-cellulose, DEAE-cellulose, and AE-cellulose. DEAE-Sephadex A-50 is a suitable anion exchange dextran. The pH is maintained between about 6.0–10.5, preferably between about 6.5–10.0, to allow preferential adsorption of albumins to the resin, leaving a substantially albumin-free lysozyme extract. The lysozyme must be desalted prior to ion exchange. A double-bed ion exchange for desalting and extraction uses a cation exchange resin followed by an anion exchange resin. This method maintains lysozyme activity even at low pH, where activity would otherwise be irreversibly reduced.

Muzzarelli discloses the preferential, reversible adsorption of lysozyme on chitosan. The chitosan is not hydrolyzed by the lysozyme. Muzzarelli suggests eluting the chitosan with a propylamine solution and suggests pretreating HEW with sulfuric acid prior to adsorption on the chitosan to eliminate high molecular weight egg-white proteins. The albumin fraction is irreversibly damaged with this process.

Jensen and Kleppe disclose an affinity between lysozyme and chitin, but show that lysozyme destroys the chitin resin by hydrolyzing the N-acetyl-D-glycosamine residues of the chitin.

Cherkasov discloses a method of separating lysozyme from HEW by diluting the HEW, adjusting the pH to 5.5, and contacting the treated solution with chitin powder at a pH between 5.0 and 5.5 and an ion strength greater than or equal to 0.1. Cherkasov teaches that at pH 7.9–8.0, lysozyme complexes with chitin to strongly bind to the chitin resin and the affinity can only be broken with dilute acid, such as 0.1M acidic acid.

Weaver discloses that deaminated chitin has a high specificity and capacity for lysozyme. Deaminated chitin has a good stability for isolating lysozyme and allows fast flow rates.

Tosa discloses that kappa-carrageenan is a polysaccharide composed of unit structures of beta-D-galactose sulfate and 3,6-anhydro-alpha-D-galactose, having a molecular weight of around 100,000–800,000 Daltons and an ester content of 20–30%. The article details that kappa-carrageenan is a suitable polysaccharide for immobilization of enzymes and microbial cells in its gel lattice. As described by Chibata, kappa-carrageenan shows a unique ability to bind with and to stabilize proteins. Binding of proteins is primarily due to half-ester sulfate groups, which are strongly anionic, being comparable with sulfuric acid. The action is considered to be electrostatic ion exchange. Treating the kappa-carrageenan with tannin blocks the sulfate groups to provide a treated carrageenan which is also usable as a specific adsorbent for proteins. Specifically, adsorption of glucoamylase on tannin-carrageenan beads occurred with an increased absorption capacity than other tannin-treated polysaccharides.

Agarose is a polysaccharide useful for binding of lysozyme and other proteins, and comprises (1,3)N-beta-D-galactopyranose-(1,4)N-3,6-anhydro-alpha-D-galactose. Chitosan is a polysaccharide essentially being a polymer of glucosamine subunits.

DISCLOSURE OF INVENTION

The present invention relates to a commercial method for separating lysozyme from egg-white without destroying the commercial utility of the lysozyme or the remaining egg-white fraction by use of an affinity resin to preferentially, reversibly bind the lysozyme.

Lysozyme will bind a hexasaccharide in a cleft in the middle of the lysozyme molecule. Many different polysaccharides will bind with differing affinities for elution. Some polysaccharides will be hydrolyzed upon binding and will be broken into smaller fragments. For example, chitin is hydrolyzed, while chitosan is not. The present invention relates to preparation of a resin which will preferentially, reversibly bind lysozyme but not be hydrolyzed by the lysozyme. To prepare the resin, the dry powders of the suitable polysaccharides are mixed together and are then slowly added with vigorous stirring to water at a temperature of about 70°–85° C. Between about 3.5–6.0% powder is added to the water, with the most typical resin gel having about 5.0% dry solids. After all the powder has dissolved, the solution is heated at about 80° C. for 10–15 minutes. Then, additional gelling agents, such as 6 mM gluteraldehyde, may be added to enhance the gel formed, and the mixture is allowed to cool. The resulting gel is ground into particles or deposited to form substantially uniform particles, mixed three times with three volumes of 1M KCl and then washed with water until the conductivity of the eluant is 1000 $\mu$MHO's. The KCl wash is used for two reasons: first, the treatment makes the resin a little harder, and second, the treatment washes away undesirable polysaccharides bound to the raw resin product. KCl is used rather than NaCl because the former increases the gel strength of the resin, while the latter dissolves certain resins, such as kappa-carrageenan. The water wash is used to remove excess KCl from the resin so that when the resin is contacted with the hen egg-white (HEW), the albumin fraction of the HEW will be suitable for commercial human consumption. The preferred ratio of water to resin is approximately 2.5:1. During the water wash, the resin swells substantially.

The affinity resin is added to hen egg-white to allow the lysozyme fraction of the HEW to preferentially, reversibly bind to the resin. The binding preferably occurs at about the neutral pH of the egg-white, and the temperature is maintained below about 10° C. After contacting the resin and HEW for approximately 15–60 minutes, the albumin fraction is separated from the resin to leave the lysozyme fraction bound to the resin. The albumin fraction is removed for further processing as commercially acceptable egg-white. The resin is washed to remove unwanted proteins from the resin bound less tightly than the lysozyme. The lysozyme is then eluted from the resin by washing the resin with an aqueous KCl solution having an ion concentration of at least about 1M, and the lysozyme fraction is further treated to prepare a crystalline product of lysozyme or a salt of lysozyme, such as lysozyme chloride.

The further processing of the raw lysozyme generally includes recrystallization of the lysozyme; filtering the recrystallized lysozyme to isolate the crystals; redissolving the lysozyme and filtering the solution to remove denatured and contaminating proteins; dialyzing the filtered solution, either by electrodialysis or molecular filtration, to obtain a raw product; and purifying the raw product and spray drying it for packaging.

Affinity resins are particular polysaccharides to which the lysozyme cleft may bind. Commercially desirable, reversibly bindable affinity resins are generally derivatives of sea life polysaccharides, such as agar, agarose, kappa-carrageenan, chitosan, or mixtures thereof. Although both kappa-carrageenan and agar have a high concentration of free sulfate groups which will be negatively charged at the normal pH of HEW, these polysaccharides apparently work on an affinity basis rather than on an electrostatic (ion exchange) basis. If the resin were to act on an electrostatic basis, binding would vary with the pH of the solutions in which the resin is mixed. For example, at pH 5.5, lysozyme should bind more readily to the negative sulfate group in comparison to its binding at pH 8.5, where the net charge of the protein is approaching zero (pI is approximately equal to 10.5). However, this pH-dependency does not occur. The lack of pH-dependency cannot be attributed to blocking of the sulfate groups with conalbumin (pI=6.6) of the HEW because a peak of binding of lysozyme does not occur midway between the two pI's. Also, a marked increase in binding activity of the lysozyme with chitosan (a nonionic polysaccharide) or mixtures of chitosan and kappa-carrageenan indicates that the binding is of the chemical affinity type rather than an electrostatic interaction.

Use of an affinity resin which preferentially, reversibly binds lysozyme at about the natural pH of egg-white results in a commercially valuable system for the separation of lysozyme from hen egg-white without destroying the commercial value of either the lysozyme or the albumin fractions. This process results in a reusable resin product which allows bench scale-up of the separation process for the systematic and semicontinuous processing of large volumes of hen egg-white. The commercialization of an affinity resin-type separation process should greatly reduce the processing cost for the separation of lysozyme from egg-white.

BEST MODE FOR CARRYING OUT THE INVENTION

Figure 1:
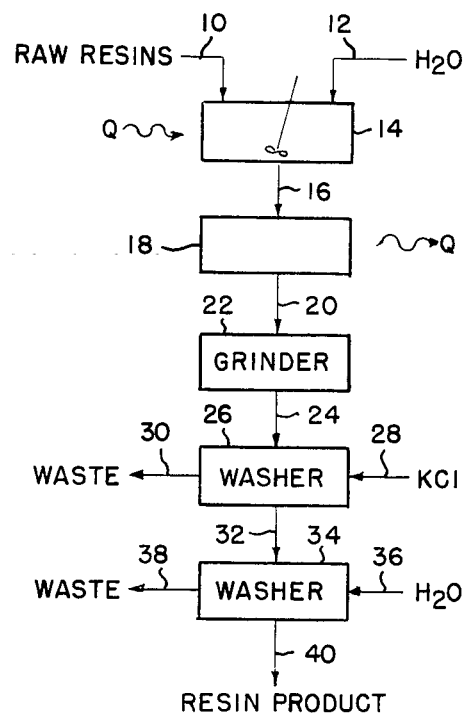
FIG. 1 is a schematic flow chart of a preferred process for making an affinity resin product.

As shown in FIG. 1, about 3.0–6.0% (w/v) raw resins, such as powdered agar, agarose, kappa-carrageenan, chitosan, or mixtures thereof are dissolved and mixed with water 12 in a heated, stirred reactor 14 at a temperature of about 70°–85° C. Usually about a 5% weight/volume, Genulacta-type P.C. carrageenan (available from Food Products, Ltd., of Vancouver, British Columbia, Canada), is made into a thick mixture in the stirred reactor 14. In some cases, KCl at about 4–10% of the weight of the carrageenan resin is added to the solution during the initial cooking of the resin. Once the resin is dissolved, the solution is heated at 80° C. for 10–15 additional minutes while the tank is continuously stirred. Additional gelling agents may be added to the mixture prior to the extended heating period. Suitable gelling agents, are for example, 6 mM gluteraldehyde. The thickened mixture 16 is removed from the reactor 14 and is allowed to cool to form a gel. From the cooling stage 18, the gelled resin 20 enters a grinder to form small particles of gelatinous resin having a large surface area suitable for lysozyme binding. Alternatively, the resin may be deposited to form substantially uniform particles 24. These particles 24 enter a washer 26, where 1M KCl 28 is used to remove polysaccharide impurities from the resin particles 24. The waste KCl solution 30 is discarded while the washed particles 32 are further treated in a second washing stage 34 with a water wash 36 to remove excess KCl from the resin particles 32 so that the resin particles may be used to commercially separate the lysozyme fraction from the albumin fraction of egg-white without commercially destroying the value of the albumin fraction. The water wash 36 produces a waste KCl stream 38 and a resin product 40.

As previously noted, various naturally occurring sea life polysaccharides may be used to preferentially, reversibly bind the lysozyme fraction of HEW to allow separation of the lysozyme fraction from the albumin fraction of the egg-white without commercially destroying the value of either the lysozyme fraction or the egg-white fraction. These affinity resins are typically agar, agarose, keppa-carrageenan, and chitosan. Mixtures of the raw powders may be combined and dissolved to provide raw resin products 40 which include a combination of the individual polysaccharides.

Throughout this application, such mixtures of resin products will be identified as, for example, agarose—chitosan, which is a mosaic, integral resin product 40 having a gel consisting of a portion of agarose and a portion of chitosan. The term "mixtures thereof" shall mean physical mixing of prepared particles of resin to form a resin product having individual, distinct resin particles of different resins. That is, kappa-carrageenan resin particles may be mixed with particles of pure agarose after the gelled particles are formed to make an agarose and carrageenan mixture.

Table 1 shows the activity of integral, mixed resin product particles containing kappa-carrageenan and chitosan within a single particle.

TABLE 1

| RESIN COMPOSITION | | LYSOZYME ACTIVITY EXTRACTED WITH RESIN |
|---|---|---|
| % Kappa-Carrageenan | % Chitosan | |
| 5.0 | 0 | 30 |
| 4.5 | 0.5 | 40 |
| 4.0 | 1.0 | 50 |
| 3.0 | 2.0 | 57 |

In Table 1, the resin particles included 5% total solids in the resin gel which was formed by dissolving the resins together with water. A 10% solution of the resin in HEW (v/v) was mixed for 60 minutes and eluted to determine the lysozyme activity. The table shows that mixing kappa-carrageenan and chitosan powders before formation of a resin gel surprisingly produces a particularly desirable chitosan—kappa-carrageenan resin which surprisingly extracts a much greater amount of lysozyme activity than either pure resin. It is not completely understood what produces the surprising increase in extractible lysozyme activity.

Table 2 shows tests on mixed resin particles containing kappa-carrageenan and agarose within a single particle.

TABLE 2

| RESIN COMPOSITION | | LYSOZYME ACTIVITY EXTRACTED WITH RESIN |
|---|---|---|
| % Kappa-Carrageenan | % Agarose | |
| 0.5 | 2.5 | similar to pure resins |
| 1.0 | 2.0 | similar to pure resins |
| 1.5 | 1.5 | similar to pure resins |
| 2.0 | 1.0 | similar to pure resins |
| 2.5 | 0.5 | similar to pure resins |

Increasing the concentration of agarose increased the hardness of the gels that were formed.

Tables 1 and 2 are given by way of example rather than by way of limitation to demonstrate the intended meaning of the integral resin particles of mixed dry powders. Other composite resin particles could be formed with the teachings of this invention, and they are considered to be a part of this invention. Also, the combination of integral, pure or composite, resin particles with resin particles of different chemical composition are contemplated as being suitable for the extraction of the lysozyme fraction from egg-white without commercially destroying the value of the lysozyme fraction or the albumin fraction. The resins do not chemically interact with each other or with the albumin or lysozyme fraction apart from the binding and are thought to operate independently so that mixtures of any active resin with another resin of similar activity will result in the mutual extraction of lysozyme without harm to either the lysozyme fraction or the albumin fraction. Therefore, it is considered to be redundant to include examples of the various combinations and mixtures of resin particles that might be constructed using the teachings of this invention.

Affinity resins made with agar, agarose, kappa-carrageenan, chitosan, and mixtures thereof are efficient, preferential, and reversible binders of the lysozyme fraction. For example, a mixture of 10% kappa-carrageenan resin and HEW (v/v) was stirred for 15 minutes to allow the lysozyme fraction to preferentially bind to the kappa-carrageenan resin. The kappa-carrageenan resin was a 5% resin (w/v). In a first contact of the kappa-carrageenan resin with HEW, the resin extracted 27.3% of the total lysozyme activity. The resin was washed three times with water (three volumes each), during which time 1.07% of the extracted lysozyme activity was lost. The resin was then washed with five washings of 1M KCl solution to recover 94.3% of the extracted lysozyme activity, leaving unaccounted 4.6% of the extracted lysozyme. The resin was then washed with water until it was low in conductivity (less than about 1000 μMHO's). This washed resin was then recontacted with HEW and again extracted 27.3% of the total lysozyme activity after 15 minutes of mixing. The resin was washed with water, losing 0.6% of the extracted lysozyme activity, and the extracted lysozyme was eluted from the resin with five KCl washings to recover 101.0% of the extracted lysozyme activity. In neither case was the kappa-carrageenan resin hydrolyzed by the reversible binding of lysozyme to the resin. In the two contacts, 27.3% of the total lysozyme activity was extracted, 0.84% of the lysozyme activity was lost in the water washings, while 98% of the extracted lysozyme activity was recovered in the KCl wash. 1.16% of the extracted lysozyme was unaccounted for and was probably tightly bound to the resin.

Usually the lysozyme fraction saturates the available sites for affinity binding onto the resin in about 15-60 minutes. Preferably, the resin particles are mixed with the egg-white for at least about 30 minutes to substantially saturate the resin particles. To elute the lysozyme fraction from the resin, due to the tight binding of the lysozyme to the resin, it requires at least about a 1M KCl solution to fully elute the lysozyme. When using an increasing gradient of salt solution, multiple fractions are extracted. These functions may reflect a heterogeneity of the lysozyme proteins within the egg-white itself, or heterogeneity in the resin itself. Also, to fully elute the lysozyme requires almost ten volumes of 1M KCl solution. As shown in the example, however, five washings with 1M KCl solution extract substantially all of the available lysozyme.

Figure 2:
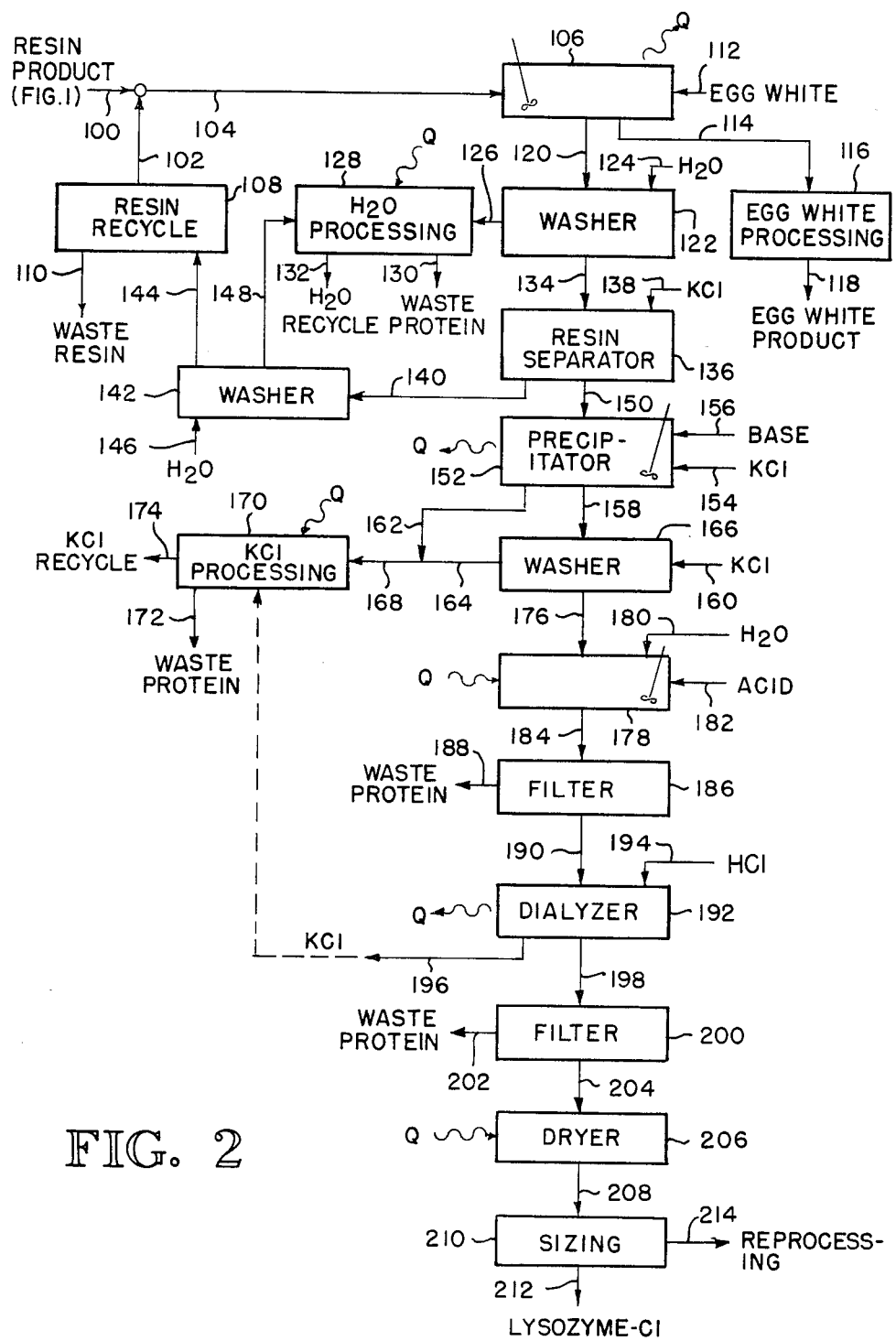
FIG. 2 is a schematic flow chart of a preferred process for separating the lysozyme fraction from egg-white and processing the lysozyme fraction to a desired product.

Now referring to FIG. 2, a resin product 100 is combined with recycled resin 102 to form a charge resin 104 which is placed within a reaction vessel 106, such as a stirred reactor or packed column. The recycled resin 102 is charged from a storage treatment tank 108, where waste resin 110 is removed from the system.

In the typical commercial process, hen egg-white (HEW) 112 is charged to the reactor 106. The egg-white 112 and resin charge 104 are continuously stirred within the refrigerated reactor 106 for between 15-60 minutes to allow the lysozyme fraction to preferentially, reversibly bind to the resin charge 104 and to substantially saturate the available sites for lysozyme binding on the resin.

Through centrifuging and decanting, the albumin fraction of the egg-white is removed from the resin which has lysozyme bound to it, and the albumin fraction 114 passes to egg-white processing stages 116 to prepare a commercially acceptable egg-white product 118. The resin-lysozyme complex 120 enters a washing stage 122, where water 124 is used to remove excess proteins of the albumin fraction and unwanted and contaminating proteins or polysaccharides. The waste solution 126 from the washer 122 passes into a waste-processing unit 128 where the pH is adjusted to 3.0-4.0. Then, the solution is heated to denature the proteins within the solution so that waste proteins 130 can be removed and discarded while the water 132 may be recycled, after its pH is readjusted to about 7.0. The washed resin-lysozyme complex 134 is further washed in a resin-lysozyme separation stage 136 with at least 1M KCl 138 in serial washes to elute the bound lysozyme from the resin. The clean resin 140 is further washed in a washer 142, and the washed resin 144 is passed to resin recycle treatment and storage tank 108. The water 146 for the wash forms a waste-water stream 148 which enters the water processing unit 128 previously described.

The eluted lysozyme fraction 150 enters a precipitator stage 152 in which the concentration of the KCl in solution is increased by the addition of solid KCl 154 (or addition of concentrated KCl solution) to the lysozyme eluant to form a 0.7-1.5M KCl (preferably 1.0M KCl). The pH of the solution is adjusted to about the isoelectric point (pI=10.5) by addition of base 156, such as KOH. Also, the slowly stirred solution is cooled to about 5° C. Crystals of lysozyme form, and these crystals 158 are washed with a KCl solution 160 to remove any undesired impurities. The waste solutions 162 and 164 from the precipitation stage 152 and KCl washing stage 166 are combined into a single waste stream 168, which undergoes KCl processing (principally through the addition of heat to denature undesired proteins) to form a waste protein stream 172, which is discarded, and a recyclable KCl solution 174.

The washed lysozyme crystals 176 are redissolved in a mixer 178 by making approximately a 7–15% solution of lysozyme in water 180 while adjusting the pH to about 3.5 with acid 182, such as HCl, and the addition of heat. Resulting solution 184 is filtered in a press filter 186 to remove contaminating or denatured proteins 188 prior to passing the filtered lysozyme solution 190 to a dialyzer 192. The dialyzer may be an electrodialyzer, such as the DU-Ob Ashai Glass Company dialyzer, or may be a molecular filtration dialyzer. With electrodialysis, the pH of the solution is maintained at less than about 5.0 by periodic additions of acid 194, such as HCl. Preferably, the pH of the solution is maintained in a range of about 3.0–4.0, and the dialysis occurs at temperature maximum of no greater than about 5° C. A concentrated KCl solution 196 is formed in the dialyzer 192 (where desalting occurs), and this concentrated KCl solution 196 may be passed to the KCl processing stages 170. The dialyzed solution 198 passes through an antimicrobial microfilter 200 (pore size approximately 0.45 microns) to remove bacteria and denatured or contaminating waste proteins 202 prior to entry of the purified lysozyme solution 204 into spray dryer 206, where crystalline lysozyme or crystalline lysozyme chloride is formed. This crystalline product 208 is sized in suitable sizing equipment 210 to form product lysozyme chloride 212 and reprocessing lysozyme crystals 214.

In this manner, a commercial lysozyme product 212 and a commercial dried albumin fraction egg-white product 118 may be readily formed with recycling of the affinity resin which promotes the separation of lysozyme from the egg-white.

While described as a batch process for the contacting of the precycled resin with the egg-white, a continuous method for the extraction of the lysozyme fraction from the egg-white is contemplated and preferred by the use of belt filters to separate the resin from the egg-white.

I claim:

1. A method for separating lysozyme from egg-white which has a lysozyme fraction and an albumin fraction, without destroying the commercial utility of the lysozyme fraction or the albumin fraction, comprising the steps of:
    (a) preferentially, reversibly binding the lysozyme fraction to an affinity resin at about the natural pH of the egg-white by contacting the egg-white with the resin;
    (b) separating the albumin fraction from the resin to leave the lysozyme fraction bound to the resin and to obtain an albumin fraction of commercial value; and
    (c) eluting the bound lysozyme from the resin to obtain a lysozyme solution and a reusable resin.

2. A method for separating lysozyme from egg-white which has a lysozyme fraction and an albumin fraction, without destroying the commercial utility of the lysozyme fraction or the albumin fraction, comprising the steps of:
    (a) charging the egg-white to a stirred reactor;
    (b) preferentially, reversibly binding the lysozyme fraction to an affinity resin by immersing the resin within the egg-white at about the natural pH of the egg-white;
    (c) filtering the mixture of resin and egg-white to separate the resin from the albumin fraction;
    (d) removing the albumin fraction from the resin to leave the lysozyme bound to the resin and to obtain an albumin fraction of commercial value; and
    (e) eluting the bound lysozyme from the resin with a salt solution to obtain a lysozyme solution and a reusable resin.

3. A method for separating lysozyme from egg-white which has a lysozyme fraction and an albumin fraction, without destroying the commercial utility of the lysozyme fraction or the albumin fraction, comprising the steps of:
    (a) charging the egg-white to a stirred reactor;
    (b) preferentially, reversibly binding the lysozyme fraction to an affinity resin at about the natural pH of the egg-white by immersing and mixing the resin within the egg-white;
    (c) separating the albumin fraction from the resin to leave the lysozyme fraction bound to the resin and to obtain an albumin fraction of commercial value;
    (d) washing the resin to leave the lysozyme bound, but to remove undesired proteins from the resin; and
    (e) eluting the bound lysozyme from the resin with a salt solution to obtain a lysozyme fraction and a reusable resin.

4. A method for separating lysozyme from egg-white which has a lysozyme fraction and an albumin fraction, without destroying the commercial utility of the lysozyme fraction or the albumin fraction, comprising the steps of:
    (a) placing an affinity resin in a packed column;
    (b) passing egg-whites through the column to preferentially, reversibly bind the lysozyme fraction to the resin by chemical affinity;
    (c) separating the resin from the albumin fraction of the egg-white, leaving the lysozyme bound to the resin and obtaining a commercially valuable albumin fraction; and
    (d) eluting the bound lysozyme from the resin with a salt solution to obtain a lysozyme fraction and a reusable resin.

5. The method of claim 1, further comprising the step of purifying the eluted lysozyme to obtain a commercial product of the lysozyme or of a salt of the lysozyme.

6. The method of claim 5 wherein the step of purifying the eluted lysozyme includes the substeps of:
    (a) recrystallizing the lysozyme;
    (b) forming a chlorine salt solution from the recrystallized lysozyme;
    (c) dialyzing the salt solution to obtain a dialysis product;
    (d) filtering the dialysis product; and
    (e) drying the solution from the filtering step.

7. The method of claim 1 wherein the salt solution is an aqueous solution of at least about 1M KCl.

8. The method of claim 3 wherein the step of separating the resin from the albumin fraction includes the substeps of:
    (a) filtering the egg-white and resin to isolate the resin from the albumin fraction; and
    (b) removing the albumin fraction from the resin to leave the lysozyme bound to the resin.

9. The method of claim 1 wherein the affinity resin includes a resin selected from the group consisting of:
    agar,
    agarose, kappa-carrageenan,
chitosan,
agarose—kappa-carrageenan,
agarose—chitosan,
kappa-carrageenan—chitosan,
agarose—kappa-carrageenan—chitosan,
agar—kappa-carrageenan,
or mixtures thereof.

10. The method of claim 9 wherein the affinity resin includes a resin selected from the group consisting of kappa-carrageenan, chitosan, kappa-carrageenan—chitosan, or mixtures thereof.

11. The method of claim 1 wherein the affinity resin includes agarose.

12. The method of claim 1 wherein the affinity resin includes kappa-carrageenan.

13. The method of claim 1 wherein the affinity resin includes chitosan.

14. A method for separating lysozyme from egg-white which has a lysozyme fraction and an albumin fraction, without destroying the commercial utility of the lysozyme fraction or the albumin fraction, comprising the steps of:
(a) preferentially, reversibly binding the lysozyme fraction to a kappa-carrageenan-chitosan affinity resin at about the natural pH of the egg-white by contacting the egg-white with the resin;
(b) separating the albumin fraction from the resin to leave the lysozyme fraction bound to the resin and to obtain an albumin fraction of commercial value; and
(c) eluting the bound lysozyme from the resin to obtain a lysozyme solution and a reusable resin.

15. The method of claim 1 wherein the affinity resin includes agarose—kappa-carrageenan.

16. The method of claim 1 wherein the affinity resin includes agarose—kappa-carrageenan—chitosan.

17. The method of claim 1 wherein the affinity resin includes agarose—chitosan.

18. The method of claim 1 wherein the affinity resin consists of a resin selected from the group consisting of kappa-carrageenan, chitosan, agarose—kappa-carrageenan, agarose—chitosan, kappa-carrageenan—chitosan, agarose—kappa-carrageenan, chitosan, or mixtures thereof.

19. The method of claim 1 wherein the mixture of egg-white and resin is substantially well mixed until the resin is substantially saturated with proteins of the lysozyme and albumin fraction.

20. The method of claim 1, further comprising cooling the egg-white prior to contacting the egg-white with the resin.

21. A method for separating lysozyme from egg-white which has a lysozyme fraction and an albumin fraction, comprising the steps of:
(a) chilling the egg-white;
(b) preferentially binding the lysozyme fraction to an affinity resin by contacting the egg-white with the resin at about the natural pH of the egg-white while maintaining the temperature below about 10° C.;
(c) separating the albumin fraction from the resin to leave the lysozyme fraction bound to the resin and to obtain a commercially valuable albumin fraction;
(d) washing the resin to remove unwanted proteins from the resin while leaving the lysozyme bound to the resin;
(e) eluting the lysozyme from the resin by washing the resin with an aqueous KCl solution having an ion concentration of at least about 1M;
(f) crystallizing the lysozyme by increasing the salt concentration to about 0.7–1.5M KCl, adjusting the pH to about the isoelectric point, and cooling the solution to about 5° C.;
(g) filtering the chilled solution to recover crystalline lysozyme;
(h) redissolving the lysozyme to form a solution of between about 7–15% lysozyme by weight;
(i) filtering the solution to remove denatured and contaminating proteins;
(j) dialyzing the filtered solution at a pH of less than 5.0 to isolate lysozyme chloride;
(k) filtering the lysozyme chloride to obtain a filtered product solution; and
(l) drying the filtered product solution to obtain powdered lysozyme chloride.

22. The method of claim 21 wherein the step of redissolving the lysozyme includes the substep of heating the solution to a temperature no greater than about 70° C. to promote dissolution of the lysozyme without denaturing.

23. The method of claim 21 wherein the step of dialyzing includes the conditions of a maximum temperature of about 5° C. and a solution pH range of about 3.0–4.0.

24. The method of claim 23 wherein the pH is maintained in the range by the periodic addition of HCl to the solution.

25. The method of claim 21, further comprising the step of recycling the KCl solution for elution.

26. The method of claim 25 wherein the recycling step includes the substeps of:
(a) heating the KCl solution to denature proteins within the solution; and
(b) removing the denatured proteins from the solution.

27. A method for separating lysozyme from hen egg-white which has a lysozyme fraction and an albumin fraction, without destroying the commercial utility of the lysozyme fraction and the albumin fraction, comprising the steps of:
(a) chilling the hen egg-white;
(b) preferentially binding the lysozyme fraction to an affinity resin selected from the group consisting of:
agar;
agarose;
kappa-carrageenan;
chitosan;
agarose—kappa-carrageenan;
agarose-chitosan;
kappa-carrageenan—chitosan;
agarose—kappa-carrageenan—chitosan;
agar—kappa-carrageenan—chitosan;
agar—kappa-carrageenan; and
mixtures thereof
by contacting the hen egg-white with the resin at about the natural pH of the hen egg-white and at a temperature below about 10° C. for between about 15–60 minutes until the resin is substantially saturated with proteins;
(c) separating the albumin fraction from the resin to leave the lysozyme fraction bound to the resin;
(d) washing the resin with water to remove unwanted proteins from the resin while leaving the lysozyme bound to the resin;

(e) eluting the lysozyme from the resin by washing the resin with an aqueous KCl solution having an ion concentration of at least about 1M to leave a reusable resin;

(f) crystallizing the lysozyme by increasing the salt concentration to about 0.7–1.5M KCl, adjusting the pH to about the isoelectric point, and cooling the solution to about 5° C.;

(g) filtering the chilled solution to recover raw, crystalline lysozyme;

(h) redissolving the raw lysozyme to form a solution of between about 7–15% lysozyme by weight;

(i) filtering the solution to remove denatured and contaminating proteins;

(j) dialyzing the filtered solution at a pH of between about 3.0 to 4.0 and at a temperature no greater than about 5° C. to isolate lysozyme chloride;

(k) filtering the lysozyme chloride to obtain a filtered product solution; and (l) drying the filtered product solution to obtain powdered lysozyme chloride.

28. The method of claim 27 wherein the resin is selected from the group consisting of kappa-carrageenan, chitosan, and mixtures thereof.

29. The process of claim 1 wherein the egg-white is substantially undiluted when mixed with the affinity resin.

30. A method for separating lysozyme from substantially undiluted hen egg-white which has a lysozyme fraction and an albumin fraction, comprising the steps of:

(a) chilling the egg-white;

(b) preferentially binding the lysozyme fraction to an affinity resin by contacting the egg-white with the resin at about the natural pH of the egg-white while maintaining the temperature below about 10° C.;

(c) separating the albumin fraction from the resin to leave the lysozyme fraction bound to the resin and to obtain a commercially valuable albumin fraction;

(d) washing the resin to remove unwanted proteins from the resin while leaving the lysozyme bound to the resin;

(e) eluting the lysozyme from the resin by washing the resin with an aqueous KCl solution having an ion concentration of at least about 1M;

(f) crystallizing the lysozyme by increasing the salt concentration to about 0.7–1.5M KCl, adjusting the pH to about the isoelectric point, and cooling the solution to about 5° C.;

(g) filtering the chilled solution to recover crystalline lysozyme;

(h) redissolving the lysozyme to form a solution of between about 7–15% lysozyme by weight;

(i) filtering the solution to remove denatured and contaminating proteins; and (j) purifying the filtered solution to obtain a commercial product of the lysozyme or of a salt of the lysozyme.

31. The method of claim 30 wherein the affinity resin is selected from the group consisting of:
agar,
agarose,
kappa-carrageenan,
chitosan,
agarose—kappa-carrageenan,
agarose—chitosan,
kappa-carrageenan—chitosan,
agarose—kappa-carrageenan—chitosan,
agar—kappa-carrageenan,
or mixtures thereof.

32. The method of claim 31 wherein the affinity resin includes kappa-carrageenan.

* * * * *